US005485496A

United States Patent [19]
Lee et al.

[11] Patent Number: 5,485,496
[45] Date of Patent: Jan. 16, 1996

[54] GAMMA IRRADIATION STERILIZING OF BIOMATERIAL MEDICAL DEVICES OR PRODUCTS, WITH IMPROVED DEGRADATION AND MECHANICAL PROPERTIES

[75] Inventors: Keun-Ho Lee; Chih-Chang Chu, both of Ithaca, N.Y.

[73] Assignee: Cornell Research Foundation, Inc., Ithaca, N.Y.

[21] Appl. No.: 310,489

[22] Filed: Sep. 22, 1994

[51] Int. Cl.⁶ ................................................ G21K 5/00
[52] U.S. Cl. ........................................ 378/64; 378/51
[58] Field of Search ............................. 378/64, 66, 67, 378/68, 69, 51; 422/22, 23, 291

[56] References Cited

U.S. PATENT DOCUMENTS

| | | |
|---|---|---|
| 3,642,500 | 2/1972 | Shults et al. . |
| 3,758,273 | 9/1973 | Johnston et al. ............... 378/64 X |
| 4,246,904 | 1/1981 | Kaplan .......................... 606/231 |
| 4,461,298 | 7/1984 | Shalaby ......................... 606/231 |
| 4,470,416 | 9/1984 | Kafrawy et al. ................. 606/230 |
| 4,507,415 | 3/1985 | Kasai et al. . |
| 4,532,928 | 8/1985 | Bezwada et al. ................ 606/230 |
| 4,532,929 | 8/1985 | Mattei et al. ................... 606/230 |
| 4,559,945 | 12/1985 | Koelmel et al. ................. 606/230 |
| 5,012,503 | 4/1991 | Nambu et al. ................... 378/64 |
| 5,035,858 | 7/1991 | Held et al. ..................... 378/64 X |
| 5,200,158 | 4/1993 | Jacob ............................ 422/292 |
| 5,226,065 | 7/1993 | Held et al. ..................... 378/64 |

OTHER PUBLICATIONS

Med Devices Diagn Instrum Rep, 6:5, Nov. 1980, Dialog Abstract.
Shalaby, S. W., et al, Biomedical Polymers, 1, 22–25, 28–34, Hanser Publishers, New York, 1994.
Voronina, S. S., et al, USSR Academy of Science News, 723–730, May 1972.
Urban, E., et al, ASAIO Journal, 145, 154, 156, 1994.

Primary Examiner—David P. Porta

[57] ABSTRACT

Biomaterial medical devices or products, e.g., absorbable sutures or joint prostheses components, are gamma irradiation sterilized in the substantial absence of oxygen (e.g., vacuum treatment to $5 \times 10^{-6}$ torr) while being maintained at a temperature about that of liquid nitrogen, with improved strength loss resistance compared to gamma irradiation sterilization under ambient conditions.

7 Claims, 4 Drawing Sheets

5,485,496

GAMMA IRRADIATION STERILIZING OF BIOMATERIAL MEDICAL DEVICES OR PRODUCTS, WITH IMPROVED DEGRADATION AND MECHANICAL PROPERTIES

TECHNICAL FIELD

This invention is directed to irradiation sterilizing of a medical device or product made of or containing biomaterial that undergoes substantial strength loss during use on gamma irradiation sterilizing under ambient conditions and has heretofore required gas sterilizing.

BACKGROUND OF THE INVENTION

Synthetic absorbable sutures composed of biodegradable biomaterials including polyglycolic acid (e.g., sold under the tradename Dexon), copolymer of glycolide and lactide (e.g., sold under the tradename Vicryl), poly-p-dioxanone (sold under the tradename PDSII), copolymer of glycolide and trimethylene carbonate (sold under the tradename Maxon) and copolymer of glycolide and epsilon-caprolactone (sold under the tradename Monocryl) are currently sterilized by gas (ethylene oxide) sterilization because of the known adverse effect of gamma irradiation sterilization on the mechanical properties and hydrolytic degradation rate of these biomaterials. Gas sterilization is time consuming and costly. The toxicity of residual amounts of ethylene oxide in medical devices and products has been a concern and degassing is a long and tedious, costly process. The medical industry has expressed a desire to replace ethylene oxide sterilization for absorbable biomaterials, e.g., absorbable sutures, with gamma irradiation sterilization if the latter method would not significantly increase the strength loss during use of the biomaterials. However, all reported data from conventional gamma irradiation of synthetic polymeric absorbable biomaterials indicates that gamma irradiation sterilization of synthetic polymeric absorbable biomaterials would be unacceptable.

There is a similar problem for non-absorbable synthetic polymeric biomaterials, e.g., in the case of acetabular or tibia components of joint protheses made of ultra high molecular weight polyethylene, which are disadvantageously weakened by conventional gamma irradiation to the extent that gas sterilization has been required.

SUMMARY OF THE INVENTION

It has been discovered herein that medical devices or products composed of or containing absorbable as well as non-absorbable polymeric biomaterials that are significantly weakened by conventional gamma irradiation sterilization are provided with improved strength properties when gamma irradiation is carried out in the substantial absence of oxygen at very low temperatures.

This discovery is embodied in a method for gamma irradiation sterilization of a medical device or product composed of or containing biomaterial that undergoes substantial strength loss after gamma irradiation sterilizing under ambient conditions and heretofore has required gas sterilizing, said method comprising gamma irradiating said medical device or product in the substantial absence of oxygen while said device is maintained at a temperature ranging from −180° C. to −200° C., thereby to sterilize said device.

Preferably, vacuum treatment to provide $1\times10^{-5}$ torr to about $1\times10^{-7}$ torr, more preferably about $5\times10^{-6}$ torr, is utilized to provide the required substantial absence of oxygen.

Preferably, liquid nitrogen is utilized to provide the required temperature.

The term "medical device or product" is used herein to mean a device or product for human body reconstruction or which is implanted in the body to control drug release. This term includes absorbable devices and products, e.g., absorbable sutures, absorbable clips, absorbable staples, absorbable pins, absorbable rods (for repairing broken bones), absorbable joints, absorbable vascular grafts, absorbable fabrics or meshes (e.g., for hernia repair), absorbable sponges, absorbable adhesives and absorbable drug control/release devices as well as non-absorbable devices and products, e.g., acetabular or tibia components of joint prostheses, and bone cement.

The term "biomaterial" is used herein to mean a material which has properties which are adequate for human body reconstruction and/or drug control/release devices or products. The term includes absorbable materials, e.g., as in the case of absorbable sutures, as well as non-absorbable materials, e.g., in the case of prostheses components. The term "absorbable" is used herein to mean that the materials will be degraded and subsequently absorbed into a human body. The term "non-absorbable" is used herein to mean that the materials will not be degraded and subsequently absorbed into a human body.

The term "sterilization" is used herein to mean treatment that achieves the killing of all types of microorganisms.

The term "undergoes substantial strength loss after gamma irradiation sterilizing under ambient condition" is used herein to mean loss of at least 50% in tensile breaking force under ASTM specified conditions of 21° C. and 65% relative humidity as determined using an Instron Universal Testing Machine with a crosshead speed of 10 mm/min, after 10 days in phosphate buffer solution (pH of 7.44) at 37° C. after total gamma irradiation of 2 Mrad.

The term "substantial absence of oxygen" means in an atmosphere containing the amount of oxygen remaining after the vacuum treatment described above.

DETAILED DESCRIPTION

Figure 1:
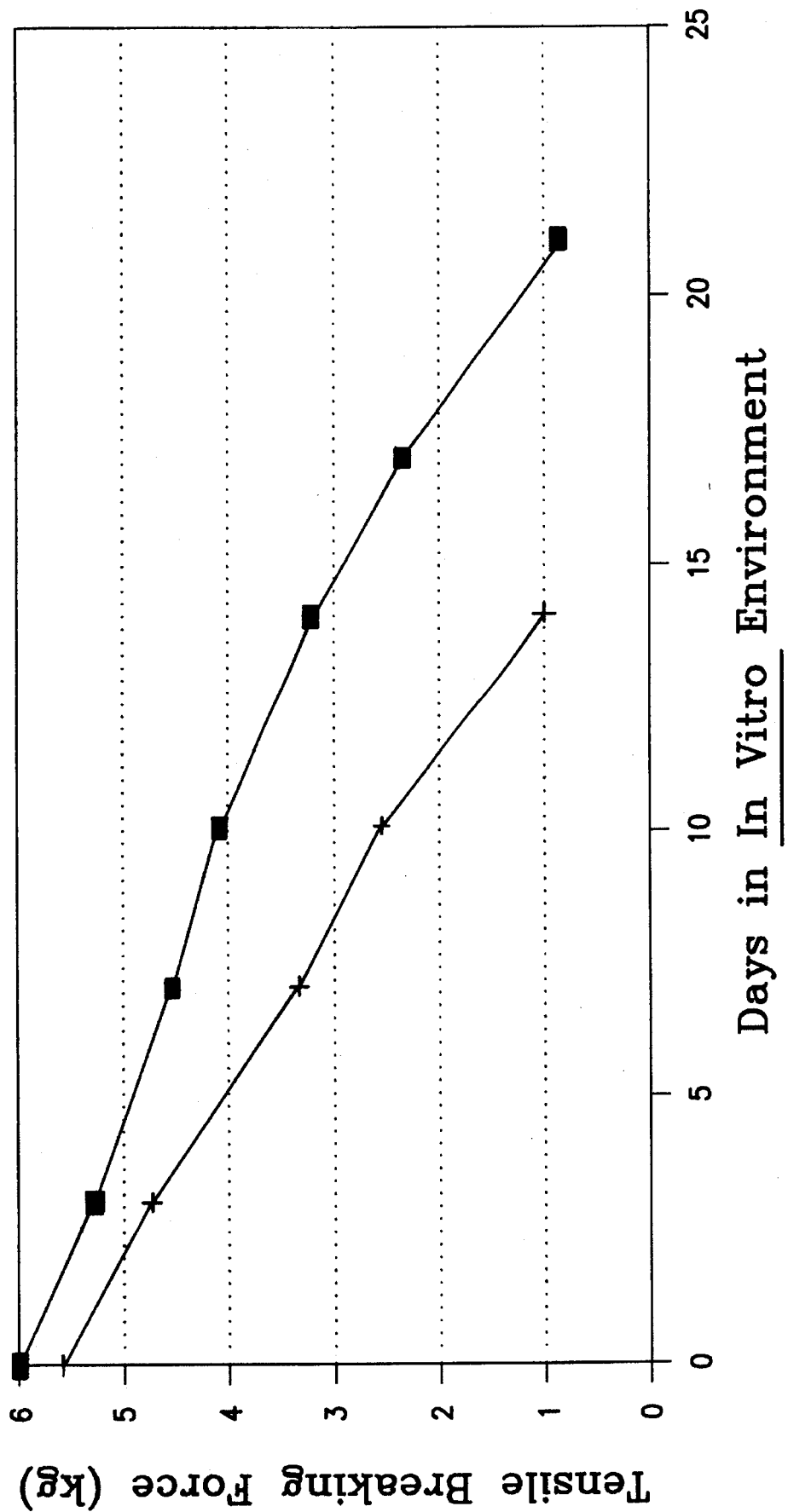
FIG. 1 is a graph of Days in Simulated Environment, i.e., in an in vitro environment, versus Tensile Breaking Force for 2–0 size absorbable sutures of Dexon gamma irradiated to 2 Mrad and shows results of Example I.

The absorbable biomaterials that constitute all or part of the medical devices or products that are advantageously treated by the invention herein are biodegradable polymers and copolymers without gamma irradiation stabilizers incorporated into the chemical structure. These include (1) biodegradable linear aliphatic homopolymer and copolymer polyesters; (2) biodegradable copolymers formed by copolymerizing (a) monomers which polymerize to form linear aliphatic polyesters with (b) monomers which do not polymerize to form linear aliphatic polyesters, or formed to be block copolymers of (a) and (b); and (3) biodegradable polymers and copolymers which do not include gamma irradiation stabilizing moieties other than (1) and (2). The weight average molecular weights of these polymers and copolymers typically range from 10,000 to 500,000, preferably from 20,000 to 125,000.

Examples of biodegradable linear aliphatic homopolymer polyesters include poly(alpha-hydroxy $C_1$–$C_5$ alkyl carboxylic acids), e.g., polyglycolic acids (e.g., sold under the tradename Dexon), poly-L-lactides, and poly-D,L-lactides; poly-3-hydroxy butyrate; polyhydroxyvalerate; polycaprolactones, e.g., poly(epsilon-caprolactone); polyglutamates; and modified poly(alpha-hydroxyacid)homopolymers, e.g., homopolymers of the cyclic diester monomer, 3-(S)[alkyloxycarbonyl)methyl]-1,4-dioxane- 2,5-dione which has the formula 4 where R is lower alkyl, depicted in Kimura, Y., "Biocompatible Polymers", in Biomedical Applications of Polymeric Materials, Tsuruta, T., et al, eds., CRC Press, 1993 at page 179.

Examples of biodegradable linear aliphatic copolymer polyesters are glycolide-lactide copolymers (e.g., sold under the trademark Vicryl), glycolide-caprolactone copolymers, poly-3-hydroxy butyrate-valerate copolymers, and copolymers of said cyclic diester monomer, 3-(S)[(alkyloxycarbonyl)methyl]-1,4-dioxane-2,5-dione, with L-lactide. The glycolide-lactide copolymers include poly(glycolide-L-lactide) copolymers formed utilizing a monomer mole ratio of glycolic acid to L-lactic acid ranging from 5:95 to 95:5 and preferably a monomer mole ratio of glycolic acid to L-lactic acid ranging from 45:65 to 95:5, e.g., a monomer mole ratio of glycolic acid to L-lactic acid of 90:10 or a monomer mole ratio of glycolic acid to L-lactic acid of 50:50. The glycolide-caprolactone copolymers include glycolide and epsilon-caprolactone block copolymer, e.g., Monocryl or Poliglecaprone.

Examples of biodegradable copolymers formed by copolymerizing (a) monomers which polymerize to form linear aliphatic polyesters with (b) monomers which do not polymerize to form linear aliphatic polyesters or formed to be block copolymers of (a) and (b) include poly(L-lactic acid-L-lysine) as described in Barrera, D. A., et al, JACS, Vol. 115, pp. 11010 to 11011 (1993); tyrosine based polyarylates, tyrosine-based polyiminocarbonates and tyrosine-based polycarbonates as described in Kohn, J., The 20th Annual Meeting of the Society of Biomaterials April 5–9, 1994 publication, page 67 and in Nathan, A., et al, "Amino Acid Derived Polymers" in Biomedical Polymers, edited by Shalaby, S. W., pages 128, 129, Hauser Publishers, New York, 1994; poly(D,L-lactide-urethanes) as described in Storey, R. F., et al, ANTEC '92, 734–737 (1992); poly(ester-amides) as described in Barrows, T. H., "Bioabsorable Poly(ester-amides)", in Biomedical Polymers, edited by Shalaby, S. W., pages 100–101, Hauser Publishers, New York, 1994; and glycolide and trimethylene carbonate block copolymer, e.g., Maxon.

Examples of other biodegradable polymers and copolymers that constitute materials of construction for medical devices or products advantageously treated by the invention herein include poly[bis(carboxylatophenoxy)phosphazene] as described in Cohen S., JACS, 112, 7832–7833 (1990); polyanhydrides, e.g., polymaleic anhydride, polysuccinic anhydride and polyglutaric anhydride; polycyanoacrylates, e.g., poly(alkyl-alpha-cyanoacrylate); and poly-p-dioxanone, e.g., PDS-II.

The non-absorbable biomaterials that constitute materials of construction for medical devices or products advantageously treated herein include ultra high molecular polyethylene, e.g., polyethylene of weight average molecular weight ranging from $1\times10^6$ to $7\times10^6$, and polypropylene.

We turn now to the provision of the substantial absence of oxygen as required in the invention herein. This is readily carried out by positioning the medical device or product to be sterilized in a gamma irradiation transparent container, e.g., a Pyrex container, and applying vacuum, e.g., using a diffusion pump, to lower the pressure to $1\times10^{-5}$ to $1\times10^{-7}$ torr, preferably to about $5\times10^{-6}$ torr, and then sealing the container, e.g., using a flame. Less preferably, the substantial absence of oxygen can be provided by positioning the medical device or product to be sterilized in a gamma irradiation transparent container and replacing air in the container with an inert gas, e.g., nitrogen, argon or helium.

We turn now to the requirement of a temperature ranging from −180° C. to −200° C. This is readily carried out by utilizing liquid nitrogen or liquid argon, e.g., by immersing oxygen depleted atmosphere container with the medical device or product therein in a gamma irradiation transparent Dewar flask or by spraying the liquified cooling gas on said container.

We turn now to the gamma irradiation treatment. This is readily carried out by positioning the medical device or product to be sterilized in a gamma irradiation sterilizing apparatus relying on $Co^{60}$ as a source of gamma irradiation. The medical device or product can be in an oxygen depleted atmosphere container in a Dewar of liquified cooling gas or the gamma irradiation sterilizing apparatus can be modified to so it contains a substantially oxygen free atmosphere (e.g., a vacuum chamber) containing a bath of liquified cooling gas or means to spray said liquified cooling gas on the device or product being sterilized. Gamma irradiation is typically applied at a rate of 0.38 to 0.45 Mrad/hr. and a sterilizing total dosage is often considered to be 2 Mrad and typically ranges from 2 Mrad to 4 Mrad.

The invention is illustrated by the following Examples.

In Examples I and II commercial medical products were utilized which had already been sterilized using ethylene oxide. The ethylene oxide treatment does not affect the strength properties of the medical products so the results of Examples I and II should be the same as if the gamma irradiation were the only sterilizing treatment.

EXAMPLE I

The manufacturer's sealed packs of 2–0 size absorbable suture thread composed of Dexon were opened and 5 inch lengths were cut and each 5 inch length was placed in a 3 mm/5 mm (i.d./o.d) Pyrex tube. Dry vacuum was drawn on each tube with a diffusion pump down to $5\times10^{-6}$ torr. Then each tube was flame sealed. The Pyrex tubes with suture thread therein were immersed in a Dewar containing liquid nitrogen (77° K. or −196° C.). The suture material containing tubes immersed in the Dewar were gamma irradiated at a dosage rate of 0.45 Mrad per hour with a total dosage of 2 Mrads or 4 Mrads. After irradiation was carried out, the tubes were removed from the liquid nitrogen and were placed in ambient surroundings overnight whereby they came to room temperature. Each tube was then broken and the irradiated suture material was removed and placed in a phosphate buffer solution (pH 7.44) and 37° C. for 3, 7, 10, 14, 17 or 21 days. The phosphate buffer solution at 37° C. simulated the in vivo environment envisioned for the medical device. The buffer solution was replaced every 2 days to ensure constant pH. Suture material samples removed from the buffer solution were vacuum dried at 25° C. overnight and then tensile breaking force was measured under ASTM Testing condition D1776-74 (21° C. and 65% relative humidity) using an Instron Universal Testing Machine with a crosshead speed of 10 mm/min.

The controls were processed the same but without the application of vacuum or immersion in liquid nitrogen, i.e., the suture material in the tubes was in contact with air at room temperature during gamma irradiation.

Figure 2:
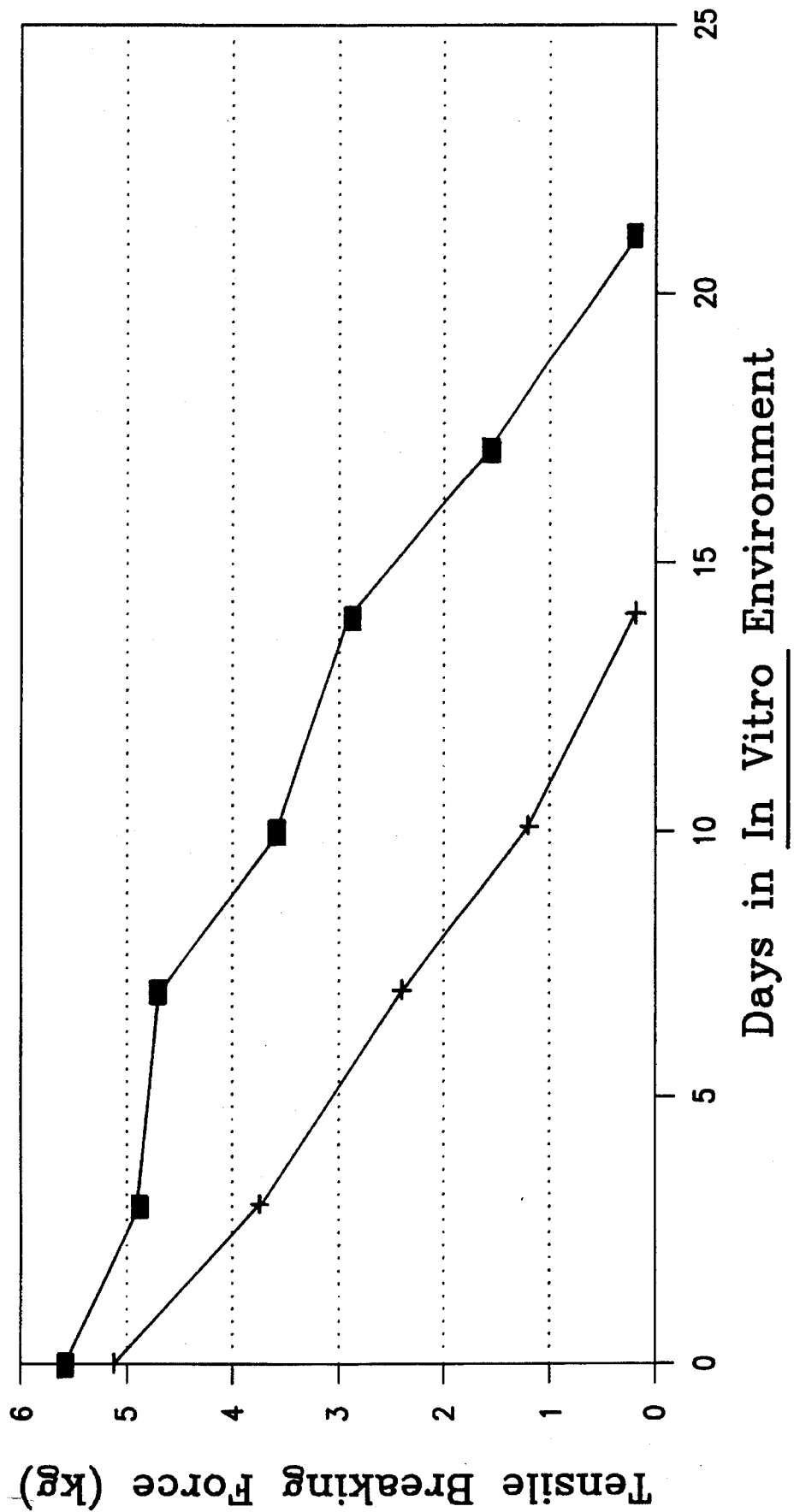
FIG. 2 is a graph of Days in Simulated Environment, i.e., in an in vitro environment, versus Tensile Breaking Force for 2–0 size absorbable sutures of Dexon gamma irradiated to 4 Mrad and shows results of Example I.

FIG. 1 shows the results for the sutures gamma irradiated with a total dose of 2 Mrad, and FIG. 2 shows the results for the sutures gamma irradiated with a total dose of 4 Mrad. The filled in rectangles are the results for the samples maintained under vacuum and in liquid nitrogen during gamma irradiation. The plus signs are the results for the samples maintained in air at 30° C. during gamma irradiation.

EXAMPLE II

The procedure of Example I was followed except that the absorbable suture thread was composed of Vicryl.

Figure 3:
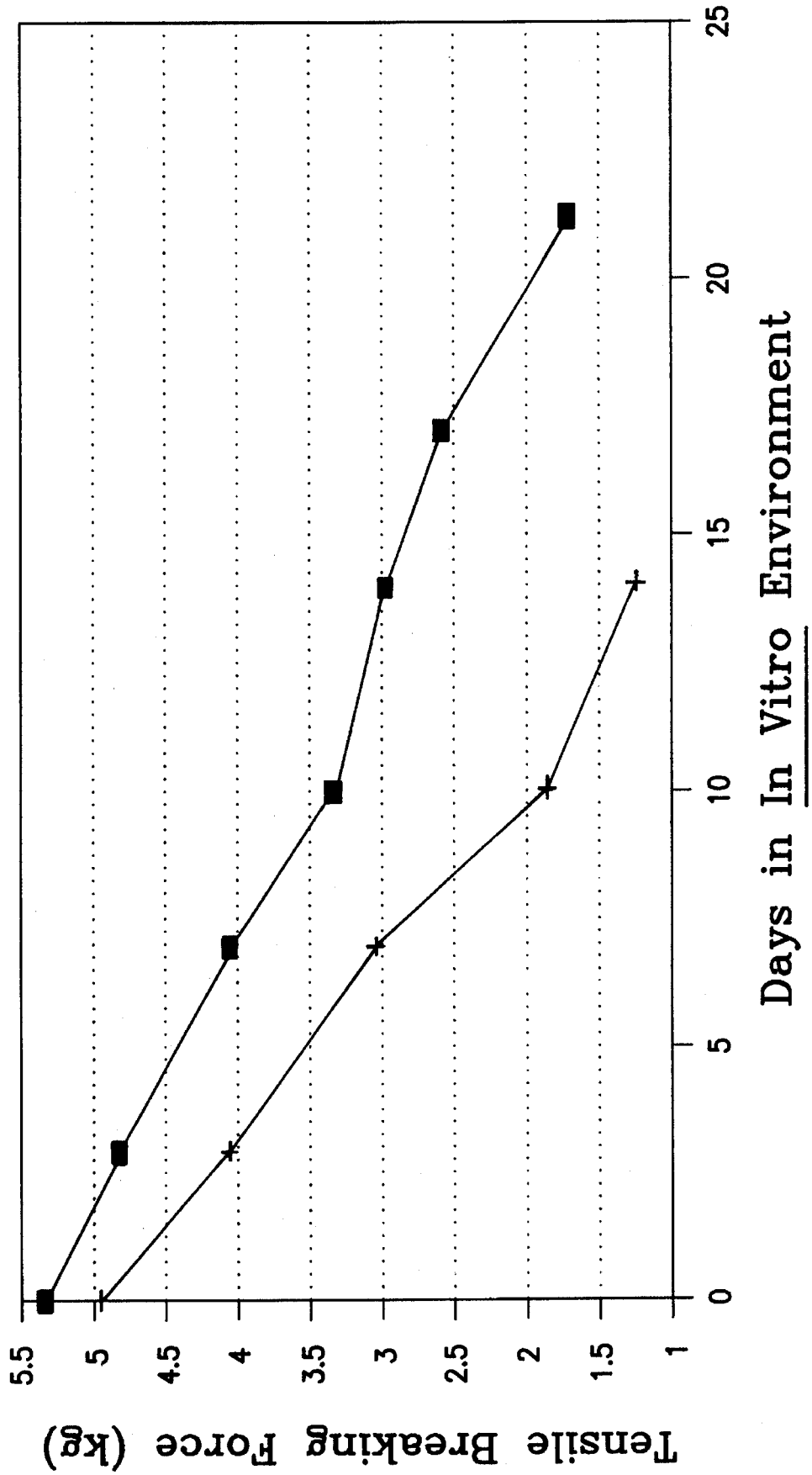
FIG. 3 is a graph of Days in Simulated Environment, i.e., in an in vitro environment, versus Tensile Breaking Force for 2–0 size absorbable sutures of Vicryl gamma irradiated to 2 Mrad and shows results of Example II.
Figure 4:
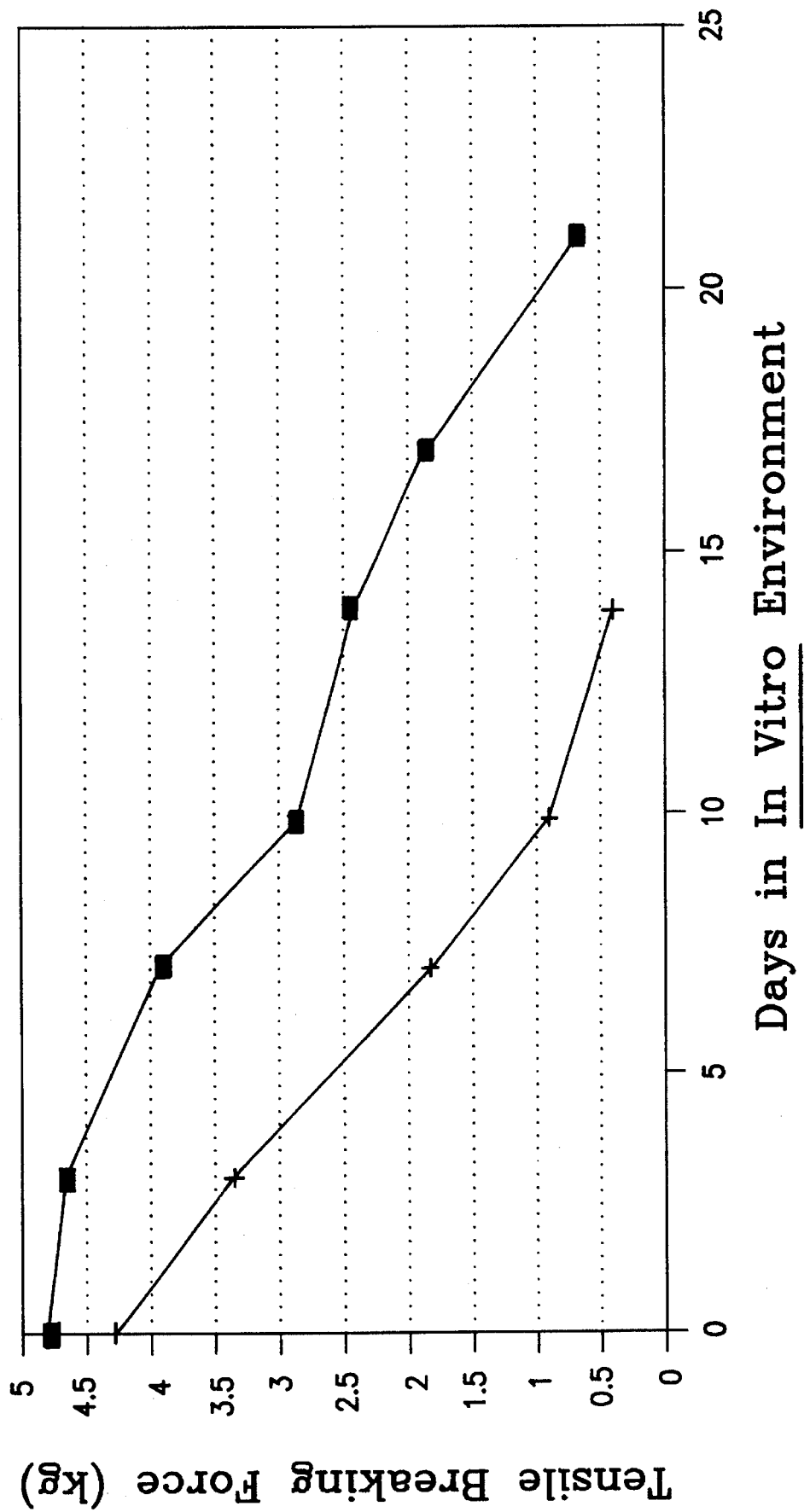
FIG. 4 is a graph of Days in Simulated Environment, i.e., in an in vitro environment, versus Tensile Breaking Force for 2–0 size absorbable sutures of Vicryl gamma irradiated to 4 Mrad and shows results of Example II.

FIG. 3 shows the results for the sutures gamma irradiated with a total dose of 2 Mrad, and FIG. 4 shows the results for the sutures gamma irradiated with a total dose of 4 Mrad. The filled in rectangles are the results for the samples maintained under vacuum and in liquid nitrogen during gamma irradiation. The plus signs are the results for the samples maintained in air at 30° C. during gamma irradiation.

EXAMPLE III

When suture material composed of PDSII is substituted for the suture material of Dexon in Example I, significantly increased resistance to strength loss over time in an in vitro environment simulating an in vivo environment, is obtained for samples gamma irradiated under vacuum and liquid nitrogen compared to controls gamma irradiated in air at 30° C.

EXAMPLE IV

When suture material composed of Maxon is substituted for the suture material of Dexon in Example I, significantly increased resistance to strength loss over time in an in vitro environment simulating an in vivo environment, is obtained for samples gamma irradiated under vacuum and liquid nitrogen compared to controls gamma irradiated in air at 30° C.

EXAMPLE V

When suture material composed of Monocryl is substituted for the suture material of Dexon in Example I, significantly increased resistance to strength loss over time in an in vitro environment simulating an in vivo environment, is obtained for samples gamma irradiated under vacuum and liquid nitrogen compared to controls gamma irradiated in air at 30° C.

EXAMPLE VI

A tibia component of a joint prostheses, composed of ultrahigh weight average molecular weight polyethylene is placed in a gamma irradiation transparent container which is evacuated to remove oxygen and then is immersed in liquid nitrogen. The tibia component in the evacuated container under liquid nitrogen is gamma irradiated at 0.45 Mrad/hr. for a total dose of 2 Mrad providing sterility. In another case, gamma irradiation is carried out in air at room temperature. The tibia component irradiated under vacuum and liquid nitrogen has significantly increased resistance to strength loss over time in an in vitro environment simulating an in vivo environment, compared to the tibia component gamma irradiated in air at 30° C.

EXAMPLE VII

Ethylene oxide sterilized absorbable sutures composed of Dexon were immersed in a suspension of Staphylococcus epidermidis ($1 \times 10^6$ cells/ml) in phosphate buffer solution at 37° C. for about 15 minutes. The sutures wee removed from immersion in the suspension and excess liquid was separated. The bacterial contaminated sutures were placed in Pyrex tubes (5 per tube) and dry vacuum was drawn on each tube overnight down to $1 \times 10^{-5}$ torr. The tubes were sealed under vacuum. The sealed tubes were immersed in liquid nitrogen. The sealed tubes at liquid nitrogen temperature were gamma irradiated with a total dosage of 2.5 Mrad. After irradiation was carried out, the tubes were removed from liquid nitrogen and were placed in ambient surroundings whereby they came to equilibrium. Then the tubes were placed inside a septic hood and opened and the sutures were removed. Of the 5 sutures from each tube, two were cultured in a bacterial culture plate wherein the bacterial culture medium was trypticase soy agar with 5% sheep blood, two were cultured in trypticase soy broth and one was reserved for scanning electron microscope examination. The culture plates and the broth with sutures therein were incubated overnight whereupon examination was carried out for bacterial growth. Six tubes were prepared and processed in this way.

Two controls were utilized. In one case, one tube was processed as above except that liquid nitrogen immersion and gamma irradiation were not carried out. In the second case, one tube was processed as above except that vacuum treatment, liquid nitrogen immersion and gamma irradiation were not carried ut.

In all the cases where the invention was utilized, there was no bacterial growth.

In the control case where vacuum was utilized, bacterial growth was noted on one of the two sutures incubated in the bacterial culture plate and on one of the two sutures incubated in trypticase soy broth.

In the control case where vacuum was not utilized, bacterial growth was noted on both sutures incubated in the bacterial culture plate and on both sutures incubated in trypticase soy broth.

Variations will be evident to those skilled in the art. Therefore the scope of the invention is determined by the claims.

What is claimed is:

1. A method for gamma irradiation sterilization of a medical device or product composed of or containing biomaterial that undergoes substantial strength loss during use if subjected to gamma irradiation sterilizing at ambient conditions, said method comprising gamma irradiating said medical device or product in the substantial absence of oxygen while said device is maintained at a temperature ranging from −180° C. to −200° C., thereby to sterilize said device.

2. The method of claim 1 wherein the medical device or product is an absorbable medical device or product.

3. The method of claim 2 wherein vacuum treatment is carried out to provide the substantial absence of oxygen.

4. The method of claim 3 wherein the vacuum treatment is to provide a pressure of $1\times10^{-5}$ torr to $1\times10^{-7}$ torr.

5. The method of claim 4 wherein the temperature is provided by immersion in liquid nitrogen.

6. The method of claim 5 wherein the absorbable medical device or product is an absorbable suture composed of polyglycolic acid.

7. The method of claim 5 wherein the absorbable medical device or product is an absorbable suture composed of copolymer of glycolide and lactide.

* * * * *